(12) United States Patent
Powell (10) Patent No.: US 6,682,910 B2
(45) Date of Patent: *Jan. 27, 2004

(54) HUMAN ERYTHROPOIETIN GENE: HIGH LEVEL EXPRESSION IN STABLY TRANSFECTED MAMMALIAN CELLS

(75) Inventor: Jerry S. Powell, Seattle, WA (US)

(73) Assignee: University of Washington, Seattle, WA (US)

( * ) Notice: Subject to any disclaimer, the term of this patent is extended or adjusted under 35 U.S.C. 154(b) by 67 days.

This patent is subject to a terminal disclaimer.

(21) Appl. No.: 10/011,858

(22) Filed: Nov. 5, 2001

(65) Prior Publication Data

US 2002/0137145 A1 Sep. 26, 2002

Related U.S. Application Data (63) Continuation of application No. 09/238,055, filed on Jan. 27, 1999, which is a continuation of application No. 08/466,412, filed on Jun. 6, 1995, which is a continuation of application No. 08/132,489, filed on Oct. 6, 1993, now Pat. No. 5,688,679, which is a continuation of application No. 07/453,381, filed on Dec. 18, 1989, now abandoned, which is a continuation of application No. 07/211,278, filed on Jun. 21, 1988, now abandoned, which is a continuation of application No. 06/879,423, filed on Jun. 27, 1986, now abandoned.

(51) Int. Cl.$^7$ ................................................. C12P 21/02
(52) U.S. Cl. ................ 435/69.1; 435/252.3; 435/254.2; 435/325; 435/352; 435/320.1; 435/69.4; 536/23.5; 536/23.51; 536/23.1
(58) Field of Search ............................... 435/69.1, 69.4, 435/252.3, 254.2, 320.1, 325, 352; 536/23.1, 23.5, 23.51

(56) References Cited

U.S. PATENT DOCUMENTS

| | | | |
|---|---|---|---|
| 4,377,513 A | 3/1983 | Sugimoto et al. | 530/395 |
| 4,703,008 A | 10/1987 | Lin | 435/360 |
| 4,751,084 A | 6/1988 | Feder et al. | 424/94.64 |
| 4,835,260 A | 5/1989 | Shoemaker | 530/397 |
| 5,441,868 A | 8/1995 | Lin | 435/69.4 |
| 5,688,679 A | 11/1997 | Powell | 435/352 |

FOREIGN PATENT DOCUMENTS

| | | |
|---|---|---|
| EP | 0 255 231 B1 | 2/1988 |
| WO | 85/02610 | 6/1985 |

OTHER PUBLICATIONS

Powell et al, Proc. Natl. Acad. Sci. USA 83: 6465 (1986).*
Tsuda et al, Eur. J. Biochem. 188: 405 (1990).*
Lin et al., "Cloning and Expression of the Human Erythropoietin Gene", Proc. Nat'l. Acad. Sci., vol. 82, No. 22, 7580–7584 (1985).
Jelkmann, "Renal Erythropoietin: Properties and Production", Rev. Physiol. Biochem. Pharmacal., vol. 104, 140–149 (1986).
Werner et al., "Purification of Proteins Produced by Biotechnological Process", Arzneim./Forsch./Drug Res., vol. 38, No. 3, 422–428 (1988).
Congote, "Effects pf Erythropoietin on Uridine Metabolism in Cell Cultures of Fetal Calf Liver", Can. J. Biochem. Cell Biol. vol. 62, Nos. 2 and 3, 143–149 (1984).
Krystal et al., "GM Affi–Gen Blue Chromatography of Human Uridine: A Simple One–Step Procedure for Obtaining Erythropoietin Suitable for in Vitro Erythropoietin Progenitor Assays", British Journal of Hematology, vol. 58, No. 3, 533–546 (1984).
Broudy et al., "Recombinant Human Erythropoietin: Purification and Analysis of Carbohydrate Linkage", Archives of Biochemistry and Biophysics, vol. 265, No. 2, 329–336 (1988).
Quelle et al., "High–Level Expression and Purification of a Recombinant Human Erythropoietin Produced Using a Baculovirus Vector," Blood, vol. 74, No. 2, 652–657 (1989).
Yanagi et al., "Recombinant Human Erythropoietin Produced by Namalwa Cells", DNA, vol. 8, No. 6, 419–427 (1989).
Lee–Huang et al. "The Human Erythropoietin–Encoding Gene Contains a CAAT box, TATA boxes and Other Transcriptional Regulatory Elements in its 5' Flanking Region", Gene, vol. 128, No. 2, 227–236 (1993).
Thompson et al., Induction of Tyrosine α–Ketoglutarate Transminase by Steroid Hormones in a Newly Established Tissue Culture Cell Line, Proc. Nat'l. Acad. Sci., vol. 56, No. 1, 296–303 (1966).
Busby et al., "Expression of Active Human Factor IX in Transfected Cells", Nature, vol. 316, No. 6025, 271–273 (1985).
Nimtz et al., Structures of Sialylated Oligosaccharide of Human Erythropoietin Expressed in Recombinant BH–21 Cells:, Eur. J. Biochem. vol. 213, No. 1, 39–56 (1993).
Interference No. 102, 334, Fritsch V. Lin, Board of Patent Appeals and Interferences, 1739–1742 (1992).
McDonald et al., "Recovery of Thrombopoietin During Purification", Biochemical Medicine and Metabolic Biology, vol. 37, 335–343 (1987).
Baig, "Purification of Human α–Fetoprotein", Analytical Biochemistry, vol. 101, 200–203 (1980).
Hearn, "General Strategies in the Separation of Proteins by High Performance Liquid Chromatographic Methods", Journal of Chromatography, vol. 418, 3–26 (1987).

(List continued on next page.)

Primary Examiner—James Martinell
(74) Attorney, Agent, or Firm—Senniger, Powers, Leavitt & Roedel (57) ABSTRACT

The Apa I restriction fragment of the human erythropoietin gene, for producing high titers of biologically active hormone from stably transfected cell lines.

10 Claims, 3 Drawing Sheets

OTHER PUBLICATIONS

Sytkowski et al., Biological Activity and Structural Stability of N–Deglycosylated Recombinant Human Erythropoietin, Biochemical/and Biophysical Research Communications, vol. 176, No. 2, 698–703 (1991).

Miyake et al., "Purification of Human Erythropoietin", Journal of Biological Chemistry, vol. 252, No. 15, 5558–5564 (1977).

Nimtz et al., "Identification and Structural Characterization of a Mannose–6–Phosphate Containing Oligomannosidic N–Glycan from Human Erythropoietin Secreted by Recombinant BHK–21 Cells", FEBS Letters, vol. 365, 203–208 (1995).

Maniatis et al., "Molecular Cloning: A laboratory Manual", 1982.

Berger "Methods in Enzymology", Guide to Molecular Cloning Techniques, vol. 152, 696–697, 1987.

New England Biolabs Catalog, 1995 p. 14.

* cited by examiner

```
CCCGGTGTGG TCACCCGGCG CGCCCCAGT  CGCTGAGGGA CCCCGGCCAG GCGCGGAGAT GGGGGTGCAC GGTGAGTACT CGCGGGCTGG GCGCTCCCGC
CCGCCCGGGT CCCTGTTTGA GCGGGGATTT AGCGCCCCGG CTATTGGCCA GGAGTGGCT  GGGTTCAAGG ACCGGCGACT TGTCAAGGAC CCCGGAAGGG
GGAGGGGGT  GGGGCAGCCT CCACGTGCCA GCGGGGACTT GGGGGAGTCC TTGGGGATGG CAAAAACCTG ACCTGTGAAG GGGACACAGT TTGGGGGTTG
AGGGGAAGAA GGTTTGGGGG GTTCTGCTGT GCCAGTGGAG AGGAAGCTGA TAAGCTGATA ACCTGGGCGC TGGAGCCACC ACTTATCTGC CAGAGGGAA
GCCTCTGTCA CACCAGGATT GAAGTTGGC  GATGCTGGTA GCCTGGGGGT GGGGTGTGCA CACGGCAGCA GGATTGAATG AAGGCCAGGG
AGGCAGCACC TGAGTGCTTG CATGGTTGGG GACAGGAAGG ACGAGCTGGG GCAGAGACGT GGGGATGAAG GAAGCTGTCC TTCCACAGCC ACCCTTCTCC
CTCCCCCGCT GACTCTCCAG CTGGCTATCT GTTCTAGAAT GTCCTGCCTG GCTGGGCTT  CCCTCTGCCT TGCTGTCGCT CCCTCTGGGC CTCCCAGTCC
TGGGCGCCCC ACCACGCCTC ATCTGTGACA GCCGAGTCCT CTCTTGGAGG CCAAGAAGGC CGAGAATATC ACGGTGAGAC CCCTTCCCCA
GCACATTCCA CAGAACTCAC GCTCAGGGCT TCAGGGAACT CCTCCCAGAT CCAGGAACCT GGCACTTGGT TTGGGGTGGA GTTGGGAAGC TAGACACTGC
CCCCTACAT  AAGAATAAGT CTGGTGGCCC CAAACCATAC CTGGAAACTA GGCAAGGAGC AAAGCCAGCA GATCCTACGC CTGTGGCCAG GGCCAGAGCC
TTCAGGGACC CTTGACTCCC CGGGCTGTGT GCATTTCAGA CGGGCTGTGC TGAACACTGC AGCTTGAATG AGAATATCAC TGTCCCAGAC ACCAAAGTTA
ATTTCTATGC CTGGAAGAGG ATGGAGGTGA GTTCCTTTTT TTTTTCTTTT CCTTTCTTTT GGAGAATCTC ATTTGCGAGC CTGATTTTGG ATGAAAGGA
```

Fig. 1A

```
GAATGATCGA GGGAAAGGTA AAATGAGACA GCAGAGATGA GGCTGCCTGG GCGCAGAGGC TCACGTCTAT AATCCCAGGC TGAGATGGCC GAGATGGGAG
AATTGCTTGA GCCCGGGAGT TTCAGACCAA CCTAGGCAGC ATAGTGAGAT CCCCATCTC TACAAACATT TAAAAAAATT AGTCAGGTGA AGTGGTGCAT
GGTGGTAGTC CCAGATATTT GGAAGGCTGA GGCGGGAGGA TCGCTGGAGC CCAGGAATTT GAGGCTGCAG TGAGCTGTGA TCACACCACT GAACTCCAGC
CTCAGTGACA GAGTGAGGCC CTGTCTCAAA AAGAAAAGA ATAATGAGGG CTGTATGAA TACGTTCATT ATTCATTCAC TCACTCACTC
ACTCATTCAT TCATTCATTC ATTCAACAAG TCTTTATTGCA TACCTTCTGT TTGCTCAGCT TGGTGCTTGG GGCTGCTGAG GGGCAGGAGG GAGAGGGTGA
CATCCCCTCAG CTGACTCCCA GAGTCCACTC CCTGTAGGTC GGGCAGCAGG CCGTAGAAGT CTGGCAGGGC CTGGCCCTGC TGTCGGAAGC TGTCCTGCGG
GGCCAGGCCC TGTTGGTGAA CTCTTCCCAG CCGTGGGAGC CCCTGCAGCT GCATGTGGAT AAAGCCGTCA GTGGCCTTCG CAGCCTCACC ACTCTGCTTC
GGGCTCTGGG AGCCCAGGTG AGTAGGAGCG GACACTTCTG CTTGCCCTTT CTGTAAGAAG GGGAGAAGGG TCTTGCTAAG GAGTACAGGA ACTGTCCGTA
TTCCTTCCCT TTCTGTGGCA CTGCAGCGAC CTCCTGTTTC CTCCTTGGCA ATCTCCCCTC CAGATGCGGC CTCAGCTGCT CCACTCCGAA
CAATCACTGC TGACACTTTC CGCAAACTCT TCCGAGTCTA CTCCAATTTC CTCCGGGGAA AGCTGAAGCT GTACACAGGG GAGGCCTGCA GGACAGGGGA
CAGATGACCA GGTGTGTCCA CCTGGGCATA TCCACCACCT CCCTCACCAA CATTGCTTGT GCCACACCCT CCCCCGCCAC TCCTGAACCC CGTCGAGGGG
CTCTCAGCTC AGCGCCAGCC TGTCCCATGG ACACTCCAGT GCCACCAATG ACATCTCAGG GGCCAGAGGA ACTGTCCAGA GAGCAACTCT GAGATCTAAG
GATGTCACAG GGCCAACTTG AGGGCC
```

HUMAN ERYTHROPOIETIN GENE: HIGH LEVEL EXPRESSION IN STABLY TRANSFECTED MAMMALIAN CELLS

CROSS-REFERENCE TO RELATED APPLICATIONS

This application is a continuation of pending U.S. patent application Ser. No. 09/238,055, filed Jan. 27, 1999, which is a continuation of U.S. patent application Ser. No. 08/466,412, filed Jun. 6, 1995, which is a continuation of U.S. patent application Ser. No. 08/132,489, filed Oct. 6, 1993, issued Nov. 18, 1997, as U.S. Pat. No. 5,688,679, which is a continuation of U.S. patent application Ser. No. 07/453,381, filed Dec. 18, 1989, now abandoned, which is a continuation of U.S. patent application Ser. No. 07/211,278, filed Jun. 21, 1988, now abandoned, which is a continuation of U.S. patent application Ser. No. 06/879,423, filed Jun. 27, 1986, now abandoned.

This invention was made in part with Government support under Research Grants HL 16919, AM 19410, AM 01418, and CA 31615 awarded by the National Institutes of Health. The Government has certain rights in this invention.

FIELD OF THE INVENTION

This invention relates generally to the field of genetic engineering, particularly to the expression of glycoprotein products of recombinant genes, and more particularly to the expression of high levels of biologically active human erythropoietin from stably transfected cells.

BACKGROUND OF THE INVENTION

The hormone erythropoietin plays a major role in regulating erythropoiesis, the formation of red blood cells, and deficiencies of erythropoietin result in anemia. Detailed studies of the hormone and attempts at replacement therapy have been difficult due to the scarcity of purified material.

Normal production of human red blood cells requires the secretion of erythropoietin by the kidney, apparently as the mature glycoprotein. In the steady state this hormone circulates in the blood at a concentration of 10 to 18 milliunits (128–230 picograms) per milliliter, and with the stimulus of severe tissue hypoxia (oxygen deficiency) the levels may increase as much as 1000-fold. The elevated hormone level triggers proliferation and differentiation of a population of receptive stem cells in the bone marrow, stimulates hemoglobin synthesis in maturing erythroid cells, and accelerates release of red cells from the marrow into circulation, thereby increasing the red cell mass and ameliorating the hypoxic conditions. Patients with deficiencies of erythropoietin, such as those with chronic renal failure, often suffer severe anemia.

Erythropoietin is a glycoprotein of 34–38 kd with approximately 40% of its molecular weight provided by carbohydrate. At least one disulfide bridge is required for activity. Little is known about the structure of this hormone, and the details of its synthesis are not well understood. Recent isolations of cDNA and genomic clones provide opportunities to analyze control of erythropoietin production, but the expression of biologically active human erythropoietin in sufficient quantities for replacement therapy has not been achieved.

SUMMARY OF THE INVENTION

Figure 1A:
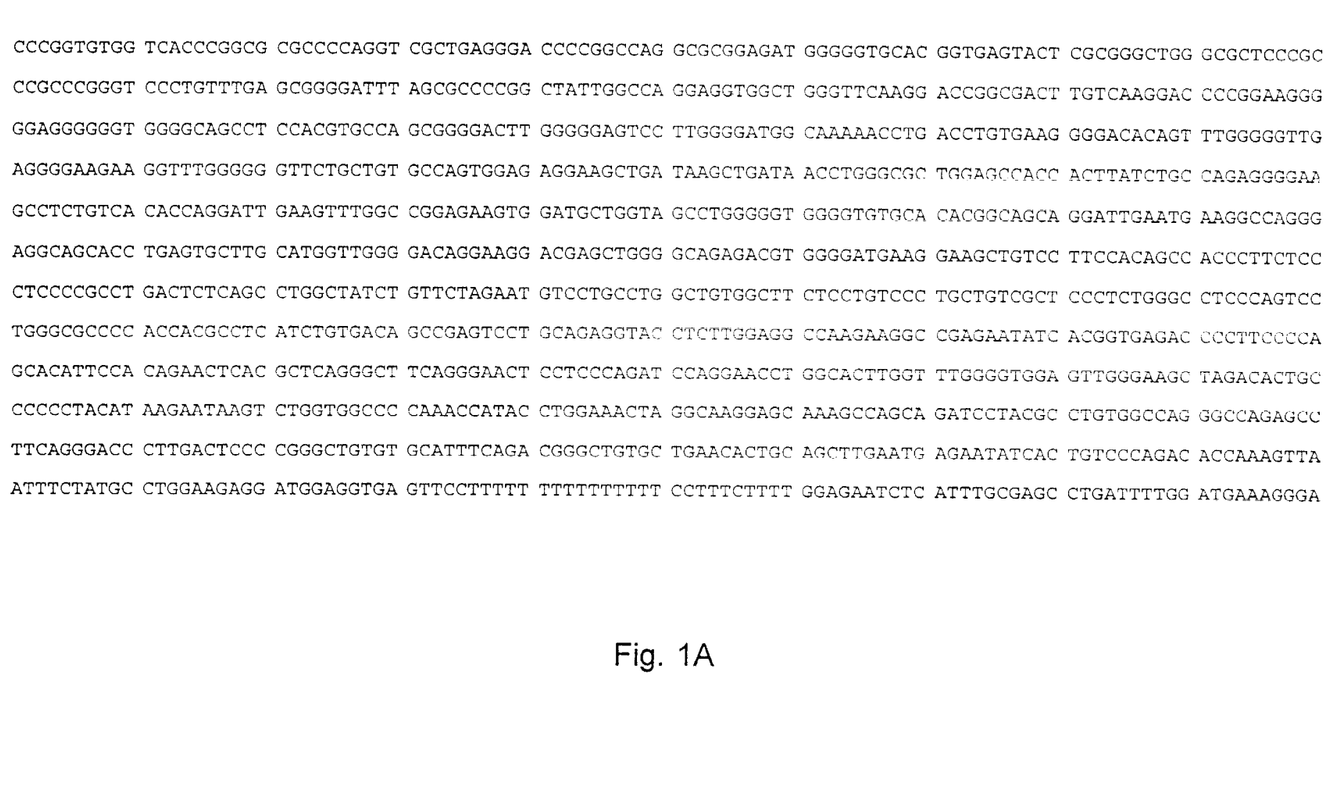
FIGS. 1A and 1B depict a schematic representation of the subject 2426 bp Apa I restriction fragment (SEQ ID NO: 1) that contains the human erythropoietin gene sequences.
Figure 1B:
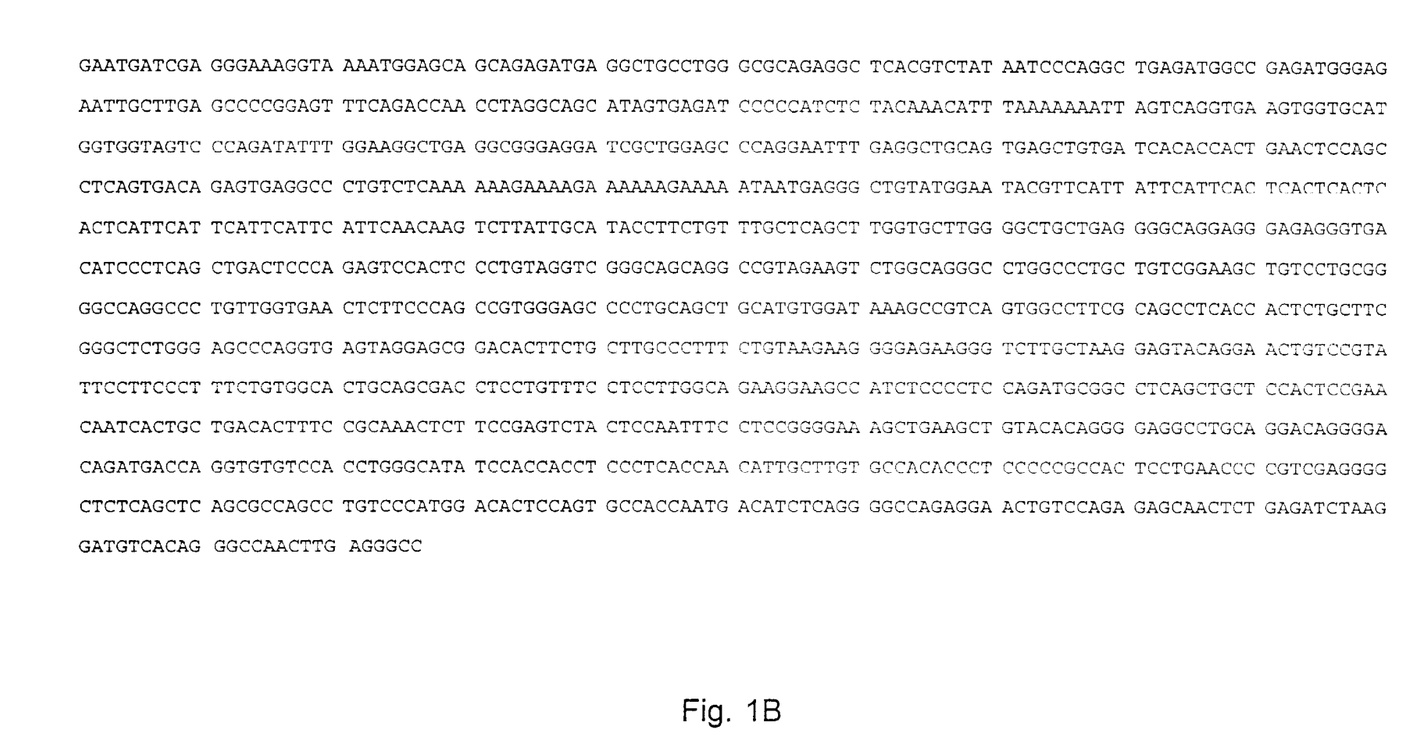

Pursuant to this disclosure, biologically active human erythropoietin can be expressed at high levels (at nominal titers exceeding two million Units per liter of supernatant) from stably transfected mammalian cell lines. Thus, an abundant source of purified human erythropoietin for clinical applications is provided. Surprisingly high expression of erythropoietin is achieved by transfecting host cell lines with the Apa I restriction fragment of the human erythropoietin gene. The sense strand of the Apa I restriction fragment has a nucleotide sequence corresponding to that shown in FIG. 1.

DETAILED DESCRIPTION OF THE PREFERRED EMBODIMENT

Figure 2:
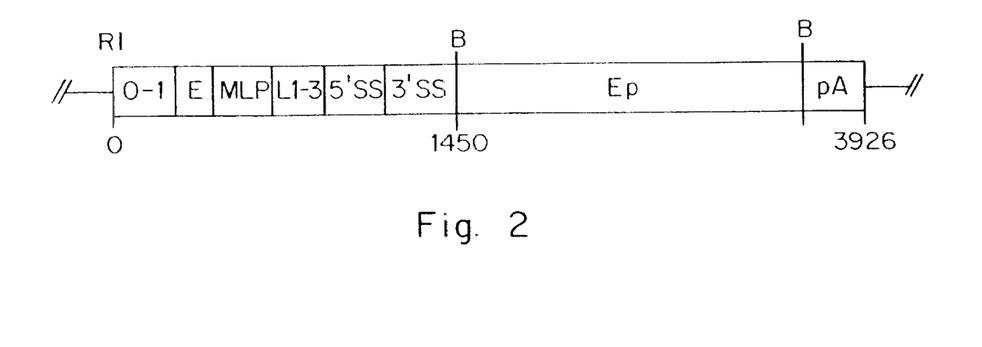
FIG. 2 depicts a representative plasmid expression vector (pD11-Ep) that contains the 2426 bp Apa I restrictione fragment; and, FIG. 3 depicts another expression vector (pBD-EP) carrying the subject Apa I restriction fragment.
Figure 3:
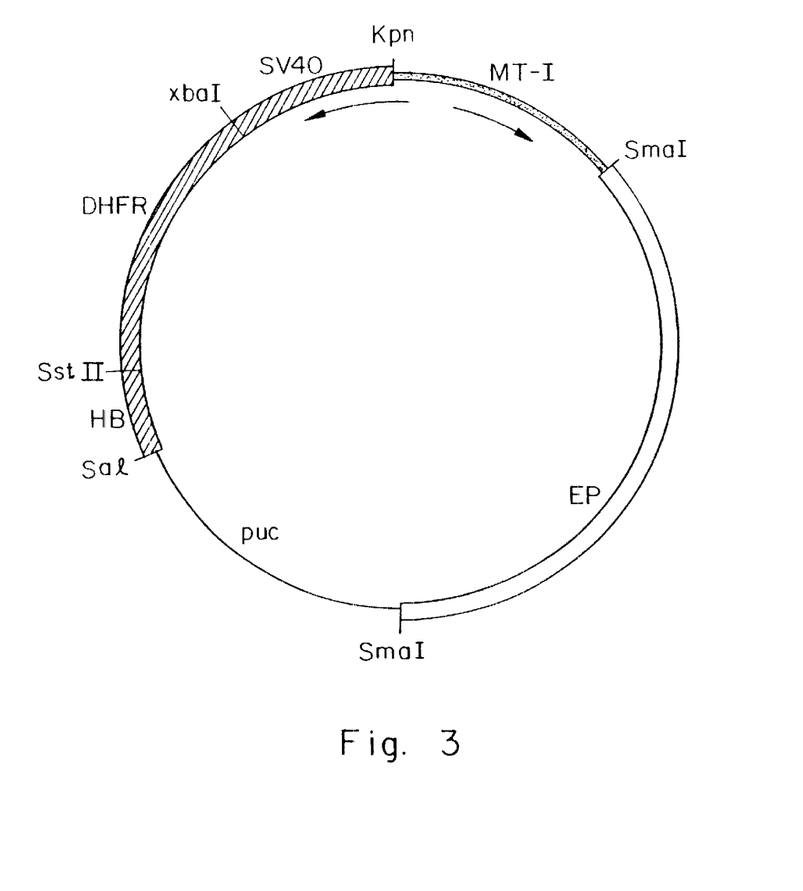

In the preferred embodiment, a genetically engineered construction of the Apa I restriction fragment shown in FIGS. 1A and 1B is inserted into a mammalian expression vector, such as those shown in FIGS. 2 and 3, and introduced into mammalian cell lines to develop stably transfected cells that produce large amounts of biologically active human erythropoietin. The Apa I restriction fragment of the human erythropoietin gene was selected to maximize efficient transcription of erythropoietin messenger RNA and effective translation and post-translational modification of the RNA into mature biologically active erythropoietin glycoprotein. Specifically, at the 5' end of the erytbropoietin gene it was important to remove interfering sequences but retain enhancing sequences. Introns were retained in the Apa I restriction fragment in order to include potentially significant enhancing sequences. At the 3' end of the gene some 3' untranslated sequences were retained to optimize putative regulating sequences. The enhanced expression provided by the Apa I fragment is demonstrated by the consistently high levels of erythropoietin expression described in the following working examples, using this fragment in concert with two promoters and two cell lines.

The following Examples are presented to illustrate the advantages of the present invention and to assist one of ordinary skill in making and using the same. These Examples are not intended in any way to otherwise limit the scope of the disclosure or the protection granted by Letters Patent hereon.

EXAMPLE 1

Isolation of Genomic Clones

A human genomic library in bacteriophage lambda (*Cell* 15:1157–1174, 1978) was screened using low stringency hybridization conditions and mixtures of oligonucleotide probes described in *Cell* 38:287–297, 1984, hereby incorporated by reference.

Oligonucleotide mixtures were prepared using an Applied Biosystems synthesizer and end-labeled using $^{32}$p-ATP and T4 polynucleotide kinase. The synthetic oligonucleotides were designed to correspond to portions of the amino terminal amino acid sequence of:

(SEQ ID NO:2)
H₂N-Ala-Pro-?-Arg-Leu-Ile-Leu-Asp-Ser-Arg-Val-Leu-Glu-Arg-

Tyr-Leu-Leu-Glu-Ala-Lys-Glu-Ala-Glu-?-Ile-Thr-Asp-Gly-Gly-Ala
                                     24 obtained by Yanagawa et al. (*J. Biol. Chem.* 259:2707–2710, 1984) for the human protein purified from urine of patients with aplastic anemia. To reduce the degeneracy of the codons for the amino acid sequence of this region, the codon usage rules of Granthem et al. (*Nucleic Acids Research* 8:43–59, 1981) and Jaye et al. (*Nucleic Acids Research* 11:2325–2335, 1983) were employed. These rules take into account the relatively rare occurrence of CpG dinucleotides in DNA of vertebrates and avoid, where appropriate, potential A:G mismatch pairings. At amino acid position 24, an asparagine was placed as most likely (*J. Biol. Chem.* 259:2707–2710, 1984). For the amino acids Glu-Ala-Lys-Glu-Ala-Glu-Asn (SEQ ID NO: 3), 2 pools of 72 sequences each were synthesized to correspond to the predicted codons. Thus, one pool was TT(c/t)TC(a/g/t)GC(c/t)TC(c/t)TT(a/g/t)-GCTTC (SEQ ID NO: 4) for the 20 nucleotide probe, and the second pool replaced a T with a C at position 18. For the amino acids Glu-Asn-Ile-Thr-Asp-Gly (SEQ ID NO: 5), one pool of sequences (AGC TCC TCC ATC AGT ATT ATT T[c/t]) (SEQ ID NO: 6) was constructed for the 23 nucleotide probe.

Plaques which hybridized to the oligonucleotide probes were rescreened at lower density until pure. After initially positive phage clones were plaque-purified, additional sequence information for the erythropoietin gene was published by Jacobs et al. (*Nature* 313:806–310, 1985). Oligonucleotides were constructed from this information and used to confirm the identity of the positive clones. After Eco RI restriction enzyme digestion of the positive clones, insert DNA was gel-purified and ligated by standard techniques into pUC 13 plasmid previously restriction-digested with Eco RI. DNA sequence was determined by dideoxynucleotide chain termination (*Proc. Natl. Acad. Sci. U.S.A.* 74:5463–5467, 1977) using dATP (α-³⁵S) and the 17-mer universal primer or, in selected regions, specific oligonucleotide primers. ³²p-ATP was from ICN; enzymes were from New England Biolabs or Bethesda Research Laboratories.

Approximately 4×10⁶ bacteriophage were screened by hybridization of replicate nitrocellulose filters. Three different clones remained positive through plaque purification, and the DNA insert was characterized by restriction mapping and partial dideoxynucleotide sequencing. Two of the three clones contained apparently complete information for the erythropoietin gene. The restriction map and sequence for the 2426 bp Apa I fragment of these clones is shown in FIGS. 1A and 1B and was essentially the same as that recently published by Jacobs et al. (*Nature* 313:806–810, 1985) for the gene for human erythropoietin gene in this amplified library, one in approximately 2×10⁶ bacteriophage, is consistent with the suggestion that erythropoietin exists as a single copy in the human genome. Southern blot hybridization of total human genomic DNA with the Apa I fragment or other restriction fragments of the erythropoietin gene indicated only a single hybridizing band with no additional regions of highly homologous DNA.

EXAMPLE 2

Selection of the Apa I Restriction Fragment

For construction of expression vectors the Apa I restriction fragment of the erythropoietin gene was obtained using techniques described in *Proc. Natl. Acad. Sci. USA* 74:5463–5467, 1967, hereby incorporated by reference. Briefly, isolated page DNA was digested with the restriction enzyme Apa I (Bethesda Research Laboratories) followed by separation on a 1% agarose gel and isolation by electroelution, phenol extraction and ethanol precipitation. The fragment was confirmed by partial sequencing as in Example 1.

Referring to FIGS. 1A and 1B, the inserted Apa I restriction fragment contained 58 bp of 5' untranslated sequences (nucleotides 0001–0058) followed by sequences coding for a putative 27 amino acid signal peptide, the mature protein, four putative intervening sequences, and 222 bp of 3' non-coding DNA sequence. At the 5' end of the gene the Apa I site is located 58 base pairs upstream from the ATG start codon (0058) for the protein sequence. The 5' site (0001) was selected to avoid a false start site just upstream from the Apa I restriction site while including putative regulatory sequence considered to be important for efficient ribosomal binding and processing. The Apa I site at the 3' end (2426) was selected to include putative processing signals in most of the 3' untranslated sequences while removing further downstream sequences. The complete erythropoietin gene, including intron sequences, was used in order to include potential regulatory or enhancing sequences located in introns that might contribute to erythropoietin gene expression or protein modification and secretion.

EXAMPLE 3

Construction of Expression Plasmids Carrying the Apa I Restriction Fragment

The 2426 bp Apa I restriction fragment containing the intact human erythropoietin gene was inserted into two expression vectors, the PD-11 and pBD constructs, each of which is based on a different mammalian promoter.

The plasmid expression vector pD11 was derived from a previously described plasmid (*Nucleic Acids Research* 13:841–857, 1985, expressly incorporated herein by reference) and contained the simian virus 40 (SV-40) enhancer sequences and origin of replication as well as the adenovirus-2 major late promoter and tripartite leader sequences. The Apa I fragment of human erytbropoietin genomic sequences (FIGS. 1A and 1B) was gel-purified, and single stranded ends were filled in by treatment with T4 DNA polymerase. Bam HI linkers were ligated to both blunt ends, and the construct was inserted into a unique 5-Bam HI restriction site of pD11 in order to direct transcription of the erythropoietin gene from a strong promoter.

The structure of the resulting expression plasmid pD11-Ep carrying the Apa I fragment (Ep) is depicted in FIG. 2. The plasmid pD11 contains 350 bp of the adenovirus left-termius (0–1), the origin and enhancer sequences from SV-40 (E), the adenovirus major late promoter (MLP), the adenovirus-2 tripartite leader (L1–3) and third leader 5' splice site (5' ss), an immunoglobulin 3' splice site (3' ss), and the late SV-40 polyadenylation signal (pA) in Eco RI (RI) restriction site of pML. Recombinant plasmids were cloned in *E. coli* HB101 and purified by isopyrenic centrifugation in cesium chloride. The expression plasmid pD11-Ep is approximately 6500 bp in length. The construction was confirmed by restriction mapping and partial dideoxynucleotide sequencing.

pBD contains the MT-I promoter sequence (Glanville, Durham & Palmiter, *Nature* 292:267–269, 1981, expressly incorporated herein by reference) and a DHFR selectable marker sequence carried in pUC plasmid. Referring to FIG. 3, the 2426 bp Apa I restriction fragment (EP) was inserted into a unique Sma I restriction site in pBD to make expression plasmid pBD-EP. The DHFR sequence in pBD-EP was associated with origin and enhancer sequences from SV40 and with Hepatitis B Surface Antigen polyadenylation sequences. pBD-EP was processed essentially as described above for pD11-EP.

While plasmid vectors were used in these confirming experiments, it is contemplated that viral or retroviral expression vectors can likewise be used to introduce the Apa I erythropoietin gene fragment into host cell lines. Suitable DNA viruses for this purpose would include adenovirus or BPV (Bovine Papilloma Virus). Suitable retroviral vectors are also known and available. It is understood that such a retroviral (RNA) vector would carry the anti-sense strand of the Apa I restriction fragment, that is, one having a sequence corresponding to the RNA transcribed from the sense strand shown in FIGS. 1A and 1B or to an allele thereof. The retroviral vector would also include sequences for transacting factors required for reverse transcription of the viral genome and integration of the DNA form of the virus into the host genome.

EXAMPLE 4

Transfection of Mammalian Cells

Each of two mammalien cell lines were transfected with each of the pD11-EP and pBD-EP constructs. Mammalian cell lines, COS-7 (monkey kidney) and BHK (baby hamster kidney), were maintained in Dulbecco's modified essential medium containing 10% fetal calf serum. Cells were passaged and when 50–70% confluent were transfected by the calcium phosphate method (*Virology* 52:456–467, 1973). BHK derives from kidney epithelial cells, generally regarded as the most likely cell that produces erythropoietin in the natural state when a mammal is anemic or hypoxic. Thus, these cells might recognize critical regulatory sequences in the Apa I fragment of the erythropoietin gene, and then effectively process and produce the erythropoietin glycoprotein.

For transient expression of cells in a 100 mm culture dish a total of 20 $\mu$g DNA was used: 10 $\mu$g of pD11-EP plasmid containing the erythropoietin gene and 10 $\mu$g of carrier salmon sperm DNA. After 48 hours the supernatant was collected, centrifuged at 400 g for 10 minutes to remove cells and debris, and frozen at −20° C. The cells were harvested separately. The results of transfections with pD11-EP alone for transient expression are shown in Table 1. Data are from 3 experiments for each cell type.

TABLE I

| Mammalian cells | Erythropoietin per ml of culture | |
|---|---|---|
| | Micrograms protein | Units (in vitro bioassay) |
| BHK | 3.4 ± 0.2 | 270 ± 16 |
| COS-7 | 3.2 ± 0.4 | 255 ± 32 |

The observed levels of erythropoietin secreted into the supernatant of either the COS-7 or BHK mammalian cell lines were approximately 80 times higher than those previously reported for transient expression of a cDNA coding for erythropoietin or for transient expression of other constructs using intact erythropoietin genes.

To establish stable cell lines producing high levels of erythropoietin, either COS-7 or BHK cells were cotransfected with the pD11-Ep plasmid and pDHFR-1a, a plasmid containing a cDNA for dihydrofolate reductase in a similar mammalian expression vector. The transfection procedure was modified so that 5 $\mu$g of pD11-Ep plasmid, 5 $\mu$g of pDHFR-1a plasmid, and 10 $\mu$g of carrier DNA were cotransfected. After additional incubation for 18–24 hours, varying concentrations of methotrexate (10 nM to 1 mM) were added to the cultures. Cells that incorporated the DHFR gene would be viable in the selective medium. After incubation for several more days, viable colonies resistant to methotrexate were isolated, passaged and screened for the presence of erythropoietin bioactivity in the supernatant. Approximately half of the methotrexate-resistant colonies that were assayed secreted detectable erythropoietin activity.

To establish stable cell lines with the expression vector pBD-EP, BHK cells were transfected by the calcium phosphate method. After 18–24 hours, these cultures were subjected to concentrations of methotrexate varying from 1 $\mu$M up to 1 mM. After incubation for several more days, viable colonies resistant to these relatively high levels of methotrexate were isolated, passaged and screened. In this series, all of the methotrexate-resistant colonies that were assayed secreted detectable erythropoietin activity.

In order to optimize the expression of the transcriptional unit containing the erythropoietin gene and the DHFR gene, BHK cell lines containing either pBD-Ep or pD11-Ep and secreting high levels of erythropoietin were passaged several times into increasing concentrations of methotrexate (*Nature* 316:271–273, 1985). However, rather than a gradual increase in the selective pressure on the cell lines by small incremental steps in the concentration of methotrexete, the cells were immediately challenged with very high levels of methotrexate (i.e., 1 mM). Only a few cells survived, but those cells would have incorporated the plasmid construction into a region of DNA particularly advantageous for expression (a so-called "hot spot") and/or would have many copies of the constructed transcriptional unit. Thus, the highest producing cell lines were selected in one step. Cell lines (including F 7.2 and S 5.2 listed in Table 2) were considered stable if erythropoietin production remained high for more than 15 passages in the absence of methotrexate selective pressure.

Amounts of erythropoietin activity in the cell pellets could not be determined due to the presence of significant inhibitors of the assay in the cell extracts. Consequently, the results shown in Table 2 do not analyze the intracellular levels of erythropoietin protein but rather the amount of erythropoietin protein produced and secreted into the supernatant by the cell lines.

TABLE 2

Expression of Recombinant Erythropoietin From
Stably Transfected BHK Cell Lines

| | Erythropoietin per ml of supernatant | |
|---|---|---|
| Cell Line | Micrograms protein | Units (in vitro bioassay) |
| pBD-EP | | |
| F 1.1 | 12.4 | 970 |
| F 3.4 | 32.0 | 2500 |
| F 6.1 | 79.6 | 6210 |
| F 7.2 | 84.1 | 6728 |
| pD11-EP | | |
| S 1.2 | 6.4 | 500 |
| S 2.4 | 64.2 | 5000 |
| S 5.2 | 82.1 | 6400 |

The observed amounts of erythropoietin secretion correspond to nominal rates of up to almost seven million Units per liter. Such nominal rates are determined by multiplying the observed yield per ml by one thousand to give an anticipated scaled-up production yield per liter.

The observed amounts of erythropoietin secretion using the Apa I fragment were on the order of 300 times greater than those previously reported (Lin et al., *Proc. Natl. Acad. Sci. USA* 82:7580–7584, November 1985) for a stably transformed CHO cell line containing a different genomic fragment of the human erythropoietin gene.

Control experiments for these transfection assays included supernatants from nontransfected cells and parallel cultures of cells transfected with plasmids containing DNA encoding other proteins, including bacterial chloramphenicol acetyl transferase and human coagulation protein, factor IX. None of the control cultures, mock transfections, or cultured cells transfected with other genes had detectable erythropoietin activity. It was also noted in the above series of experiments with the erythropoietin gene that the levels of expression obtained for selected cell lines were not related to whether the selectable marker was cotransfected along with the erythropoietin gene or was inserted into the Apa I fragment-containing plasmid prior to transfection (data not shown).

Other representative transfection methods suitable for practicing this invention include DEAE-dextran mediated transfection techniques, lysozyme fusion or erythrocyte fusion, scraping, direct uptake, osmotic or sucrose shock, direct microinjection, indirect microinjection such as via erythrocyte-mediated techniques, and/or by subjecting the host cells to electric currents. By transfection is meant the transfer of genetic information, and spectifically the information encoded by the Apa I restriction fragment of a human erythropoietin gene, to a cell using isolated DNA, RNA, or synthetic nucleotide polymer. The above list of transfection techniques is not considered to be exhaustive, as other procedures for introducing genetic information into cells will no doubt be developed. The Apa I restriction fragment will typically be operably linked (ligated) to other nucleic acid sequences such as promoter, enhancer, and polyadenylation sequences, prior to transfection. While host cell lines of mammalian origin are described, and kidney epithelial cells are considered to be particularly preferred, it is contemplated that other eukaryotic as well as prokaryotic (bacteria or yeast) host cell lines can be employed in the practice of this invention; very recent introductions of mammalian genes into plant cells offer the potential for employing plant or algal cells as well.

EXAMPLE 5

Erythropoietin Expression from Transfected Cell Lines

The recombinant erythropoietin protein secreted into the supernatant of the transfected cell lines was biologically active, and large amounts of the hormone were secreted: up to 7000 units per milliliter.

The in vitro assay for erythropoietin biological activity was based on the formation of erythroid colonies (from CPU-E; erythroid colony-forming cells) in cultures of mouse bone marrow cells in plasma clot (*Blood Cells* 4:89–103, 1978). The sensitivity of this assay is about 5 milliunits/ml. The erythropoietin used as the standard for assay was a partially purified preparation from plasma from anemic sheep (Connaught, Step 3 Ep, Lot 3026) Supernatants were assayed from passaged cell lines grown for 24 hours in fresh medium without methotrexate. The supernatant was diluted 1:200 with medium, and amounts between 1 and 10 microliters were added per milliliter of assay culture containing $2 \times 10^5$ marrow cells, 10% bovine citrated plasma, 20% fetal calf serum, 1% bovine serum albumin, and 1.6% beef embryo extract (Gibco). After incubation for 36 to 48 hours the plasma clots were fixed on microscope slides, stained with benzidine for hemoglobin, and erythroid colonies were enumerated. In the absence of added erythropoietin, no CFU-E-derived colonies were detected. Optimal erythroid colony growth (100–150 CFU-E detected per $2 \times 10^4$ marrow cells) was observed routinely with 50 mU (0.64 nanograms) etythropoietin per ml of culture. Large amounts of erythropoietin hormones were secreated into the supernatant of the transfected cell lines, see Tables 1 and 2, up to 7000 units per milliliter. Assuming the recombinant erythropoietin has a specific activity equivalent to that of natural erythropoietin (78,000 units per mg protein), the biological assay corresponds to approximately 80 $\mu$g of erythropoietin protein per milliter.

In addition, supernatants from selected cell lines were assayed for immunologically reactive erythropoietin by competitive radioimmunoassay using a polyvalent anti-human-erythropoietin rabbit anti-serum (*J. Cell. Physiol.* 118:87–96, 1984). The amount of protein measured by the radioimmunoassay was equivalent to the protein level estimated by the biological assay. These data indicate that the transfected cell lines expressed and secreted erythropoietin protein that was greater than 98% active.

The recombinant erythropoietin produced by the transfected cells was further characterized to demonstrate that these cells were secreting authentic hormone. Selected cell lines were assayed for in vivo erythropoietin activity in exhpoxic polycythemic mice (*Nature* 191:1069–1087, 1961). Supernatants secreted from the cell lines had potent in vivo biological activity when assayed in the exhypoxic polycythemic mouse. In experiments using partially purified native erythropoietin, it had been noted previously that neuraminidase treatment completely abrogated erythropoietin activity when assayed in the intact animal (*J. Biol. Chem.* 247:5159–5160, 1958). The loss of activity presumably was due to increased clearance by the liver of the desialated hormone since neuraminidase-treated erythropoietin remained fully active in vitro. The observation of potent in vivo biological activity indicates that the transfected mammalian cell lines appropriately add carbohydrate and the terminal sialic acids to the erythropoietin protein during post-translational modification.

In separate experiments, the activity of erythropoietin in the in vitro biological assay was neutralized by a neutralizing anti-human erythropoietin antibody added to the culture.

The erythropoietin secreted into the supernatant of representative transfected cell lines was also assayed for proliferative effects on other marrow progenitor cells. Recombinant erythropoietin was assayed for its effect on a variety of progenitors from mouse and human marrow including erythroid colony-forming cells (CFU-E), erythroid burst-forming cells (BFU-E), granulocyte-macrophage precursors (CFU-GM), and mixed-cell colony-forming cells (CFU-Mix) (J. Cell. Physiol. Suppl. 1:79–85, 1982; J. Cell. Physiol. 118:87–96, 1984). Erythroid stem cells exhibited a proliferation response to the recombinant erythropoietin that was parallel to the dose-response relationship found with natural erythropoietin. Neither CFU-GM nor CFU-Mix exhibited any proliferative response to the recombinant erythropoietin at concentrations up to 10 units per milliliter of assay cell culture.

When analyzed by SDS-PAGE under reducing or nonreducing conditions the purified recombinant erythropoietin electrophoresed identically to erythropoietin purified from urine of patients with aplastic anemia. Similar microheterogeneity of the proteins was observed, and the predominant species had identical molecular weights of 34 kD.

As stated elsewhere in the specification, it has been found that the recombinant human erythropoietin (rhEPO) glycoprotein of the present invention exhibits in vivo erythropoietin activity. Under the conditions of the exhypoxic polycythemic mice assay (see, e.g., Nature (1961) 191:1069–1087), values ranging from about 40,000 to about 65,000 U/mg are observed. Radioimmunassay results indicate an in vitro biological activity in the range of about 200,000 to about 240,000 U/mg. One study (see, Sytkowski, A. J. et al., in Biochem. Biophys. Res. Commun. (1991) 176(2):698–704) reports on the results of sodium dodecyl-sulfate polyacrylamide gel electrophoresis (SDS-PAGE) of the rhEPO of the invention, which shows that the glycoprotein has an average molecular weight (ca. 35 kDa) that is comparable to that found for urinary human erythropoietin glycoprotein (34–39 kDa; see, e.g., Miyake, T. et al., in J. Biol. Chem. (1977) 252:5558–5564). Additional studies under isoelectric focusing conditions show that the rhEPO of the invention comprises multiple isoforms, typically, 4–7, which reflect differing degrees of glycosylation and the nature thereof, in particular, the pattern of sialylation at available sites.

It has further been observed that the rhEPO of the invention has an O-linked oligosaccharide content of less than 1 per mole of glycoprotein. In fact, the O-linked oligosaccharide content of the glycoprotein of the present invention can be substantially less than 1 per mole of glycoprotein, and while the degree of O-glycosylation may vary from batch to batch, it is generally about 0.6 to about 0.7 per mole of glycoprotein. (See, e.g. Nimtz, M. et al., in Eur. J. Biochem. (1993) 213:39–56.)

Still further investigations on the physicochemical characteristics of the rhEPO of the present invention indicate that a phosphorylated oligomannosidic oligosaccharide moiety is present at the Asn-24 N-glycosylation site. (See, Nimtz, M. et al., in FEBS Letters (1995) 365:203–208.) (Human erythropoietin has three potential N-glycosylation sites at amino acid residues Asn-24, Asn-38 and Asn-38. There is also a potential O-glycosylation site at amino acid residue Ser-126.) And unlike urinary human erythropoietin or recombinant protein expressed by Chinese hamster ovary (CHO) host cells, rhEPO expressed by BHK host cells retains substantially all of its in vitro biological activity even after being subjected to conditions that lead to substantial, if not complete, N-deglycosylation. (See, Sytkowski, A. J. et al., in Biochem. Biophys. Res. Commun. (1991) 176(2):698–704.)

Other physiochemical properties of the recombinant human erythropoictin isolated from BHK cells provided herein are that it maintains biological activity at room temperature after prolonged storage and maintains biological activity after being reconstituted from a freeze dried state. In vitro assays show that after 6 months of storage at 25° C. in a pharmaceutically acceptable carrier or diluent, the recombinant erythropoietin obtained from BHK cells retains at least about 90% of the in vitro biologically activity as measured when originally isolated from the BHK cells. In addition, the present recombinant erythropoietin retains substantially all of its in vitro biological activity (i.e., at least 90%) when lyophilized into a powder and then reconstituted in solution with a pharmaceutically acceptable carrier or diluent. The activity of the reconstituted preparation also retains heat stability over time similar to preparations that have not been freeze dried. By contrast, recombinant human erythropoietin isolated from CHO cells loses about 90% of its in vitro biological activity after being stored for only 7 days at room temperature, and rapidly loses biological activity after being freeze dried. While not being bound by theory, it is believed the retention of biological activity over time is due to the pattern of N-linked glycosyl residues and the fact that the present erythropoietin retains biological activity after N-deglycosylation whereas erythropoietins isolated from other cells do not retain biological activity after N-deglycosylation. Studies of deglycosylated forms of these other erythropoietins, i.e., those isolated from CHO cells, shows that these molecules tend to form aggregates when exposed to heat at a neutral pH and that aggregate formation is consistently higher at alkaline and acidic pH values. (Nagai et al., J. Biochem. (Tokyo) (1992) 112(5): 700–706.

While the present invention has been described in conjunction with preferred embodiments, one of ordinary skill after reading the foregoing specification will be able to effect various changes, substitutions of equivalents, and other alterations to the compositions and methods set forth herein. It is therefore intended that the protection ngranted by Letters Patent hereon be limited only by the definition contained in the appended claims and equivalents thereof.

---

The embodiments of the invention in which an exclusive property or privilege is claimed are defined as follows:

1. Substantially pure DNA or RNA consisting essentially of nucleotide sequence corresponding to the Apa I restriction fragment of a human erythropoietin gene.

2. The DNA or RNA of claim 1 wherein the Apa I restriction fragment consists essentially of the nucleotide sequence of either the sense strand shown in FIG. 1 or the complementary RNA sequence thereof.

3. The DNA or RNA sequence of claim 1 operably linked to a second nucleic acid sequence capable of effecting expression thereof.

4. The DNA or RNA of claim 3 wherein the second nucleic acid sequence is selected from one or more of the following: promoter sequences, enhancer sequences, polyadenylation sequences, selectable marker sequences, plasmids, viral and retroviral expression vectors, and retroviral trans-acting factors.

5. Cells containing the DNA or RNA of claim 3.

6. Cells stably transfected with the DNA or RNA of claim 3.

7. Cells of claim 6 selected from the group consisting of eukaryotic cells, yeast, and bacteria.

8. Cells of claim 7 wherein the eukaryotic cells are of kidney origin.

9. Cells of claim 8 wherein the kidney cells are epithelial cells.

10. In a method of expressing recombinant biologically active human erythropoietin from a cell line in contact with an incubating medium, the improvement which comprises incorporating in said method a cell line capable of permitting a yield of erythropoietin in the incubating medium, said cell line having been produced by transfecting a host cell line with DNA, RNA, or nucleotide sequence consisting essentially of the Apa I restriction fragment of a human erythropoietin gene.

* * * * *

SEQUENCE LISTING (1) GENERAL INFORMATION:

(iii) NUMBER OF SEQUENCES: 6

-continued (2) INFORMATION FOR SEQ ID NO: 1:

(i) SEQUENCE CHARACTERISTICS:
        (A) LENGTH: 2426 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO: 1:

```
CCCGGTGTGG TCACCCGGCG CGCCCCAGGT CGCTGAGGGA CCCCGGCCAG GCGCGGAGAT      60
GGGGGTGCAC GGTGAGTACT CGCGGGCTGG GCGCTCCCGC CCGCCCGGGT CCCTGTTTG      120
GCGGGGATTT AGCGCCCCGG CTATTGGCCA GGAGGTGGCT GGGTTCAAGG ACCGGCGAC      180
TGTCAAGGAC CCCGGAAGGG GGAGGGGGGT GGGGCAGCCT CCACGTGCCA GCGGGGACT      240
GGGGGAGTCC TTGGGGATGG CAAAAACCTG ACCTGTGAAG GGGACACAGT TTGGGGGTT      300
AGGGGAAGAA GGTTTGGGGG GTTCTGCTGT GCCAGTGGAG AGGAAGCTGA TAAGCTGAT      360
ACCTGGGCGC TGGAGCCACC ACTTATCTGC CAGAGGGGAA GCCTCTGTCA CACCAGGAT      420
GAAGTTTGGC CGGAGAAGTG GATGCTGGTA GCCTGGGGGT GGGGTGTGCA CACGGCAGC      480
GGATTGAATG AAGGCCAGGG AGGCAGCACC TGAGTGCTTG CATGGTTGGG GACAGGAAG      540
ACGAGCTGGG GCAGAGACGT GGGGATGAAG GAAGCTGTCC TTCCACAGCC ACCCTTCTC      600
CTCCCCGCCT GACTCTCAGC CTGGCTATCT GTTCTAGAAT GTCCTGCCTG GCTGTGGCT      660
CTCCTGTCCC TGCTGTCGCT CCCTCTGGGC CTCCCAGTCC TGGGCGCCCC ACCACGCCT      720
ATCTGTGACA GCCGAGTCCT GCAGAGGTAC CTCTTGGAGG CCAAGAAGGC CGAGAATAT      780
ACGGTGAGAC CCCTTCCCCA GCACATTCCA CAGAACTCAC GCTCAGGGCT TCAGGGAAC      840
CCTCCCAGAT CCAGGAACCT GGCACTTGGT TTGGGGTGGA GTTGGGAAGC TAGACACTG      900
CCCCCTACAT AAGAATAAGT CTGGTGGCCC CAAACCATAC CTGGAAACTA GGCAAGGAG      960
AAAGCCAGCA GATCCTACGC CTGTGGCCAG GGCCAGAGCC TTCAGGGACC CTTGACTC     1020
CGGGCTGTGT GCATTTCAGA CGGGCTGTGC TGAACACTGC AGCTTGAATG AGAATATC     1080
TGTCCCAGAC ACCAAAGTTA ATTTCTATGC CTGGAAGAGG ATGGAGGTGA GTTCCTTT     1140
TTTTTTTTTT CCTTTCTTTT GGAGAATCTC ATTTGCGAGC CTGATTTTGG ATGAAAGG     1200
GAATGATCGA GGGAAAGGTA AAATGGAGCA GCAGAGATGA GGCTGCCTGG GCGCAGAG     1260
TCACGTCTAT AATCCCAGGC TGAGATGGCC GAGATGGGGA AATTGCTTGA GCCCCGGA     1320
TTCAGACCAA CCTAGGCAGC ATAGTGAGAT CCCCCATCTC TACAAACATT TAAAAAAA     1380
AGTCAGGTGA AGTGGTGCAT GGTGGTAGTC CCAGATATTT GGAAGGCTGA GGCGGGAG     1440
TCGCTGGAGC CCAGGAATTT GAGGCTGCAG TGAGCTGTGA TCACACCACT GAACTCCA     1500
CTCAGTGACA GAGTGAGGCC CTGTCTCAAA AAGAAAAGA AAAAGAAAA ATAATGAG      1560
CTGTATGGAA TACGTTCATT ATTCATTCAC TCACTCACTC ACTCATTCAT TCATTCAT     1620
ATTCAACAAG TCTTATTGCA TACCTTCTGT TTGCTCAGCT TGGTGCTTGG GGCTGCTG     1680
GGGCAGGAGG GAGAGGGTGA CATCCCTCAG CTGACTCCCA GAGTCCACTC CCTGTAGG     1740
GGGCAGCAGG CCGTAGAAGT CTGGCAGGGC CTGGCCCTGC TGTCGGAAGC TGTCCTGC     1800
GGCCAGGCCC TGTTGGTGAA CTCTTCCCAG CCGTGGGAGC CCCTGCAGCT GCATGTGG     1860
AAAGCCGTCA GTGGCCTTCG CAGCCTCACC ACTCTGCTTC GGGCTCTGGG AGCCCAGG     1920
AGTAGGAGCG GACACTTCTG CTTGCCCTTT CTGTAAGAAG GGGAGAAGGG TCTTGCTA     1980
GAGTACAGGA ACTGTCCGTA TTCCTTCCCT TTCTGTGGCA CTGCAGCGAC CTCCTGTT     2040
```

```
CTCCTTGGCA GAAGGAAGCC ATCTCCCCTC CAGATGCGGC CTCAGCTGCT CCACTCCG      2100

CAATCACTGC TGACACTTTC CGCAAACTCT TCCGAGTCTA CTCCAATTTC CTCCGGGG      2160

AGCTGAAGCT GTACACAGGG GAGGCCTGCA GGACAGGGGA CAGATGACCA GGTGTGTC      2220

CCTGGGCATA TCCACCACCT CCCTCACCAA CATTGCTTGT GCCACACCCT CCCCCGCC      2280

TCCTGAACCC CGTCGAGGGG CTCTCAGCTC AGCGCCAGCC TGTCCCATGG ACACTCCA      2340

GCCACCAATG ACATCTCAGG GGCCAGAGGA ACTGTCCAGA GAGCAACTCT GAGATCTA      2400

GATGTCACAG GGCCAACTTG AGGGCC                                        2426
```

(2) INFORMATION FOR SEQ ID NO: 2:

(i) SEQUENCE CHARACTERISTICS:
        (A) LENGTH: 30 amino acids
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO: 2:

```
Ala Pro Xaa Arg Leu Ile Leu Asp Ser Arg Val Leu Glu Arg Tyr Leu
1               5                   10                  15
Leu Glu Ala Lys Glu Ala Glu Xaa Ile Thr Asp Gly Gly Ala
            20                  25                  30
```

(2) INFORMATION FOR SEQ ID NO: 3:

(i) SEQUENCE CHARACTERISTICS:
        (A) LENGTH: 7 amino acids
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO: 3:

```
Glu Ala Lys Glu Ala Glu Asn
1               5
```

(2) INFORMATION FOR SEQ ID NO: 4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO: 4:

```
TTYTCDGCYT CYTTDGCTTC                                                20
```

(2) INFORMATION FOR SEQ ID NO: 5:

(i) SEQUENCE CHARACTERISTICS:
        (A) LENGTH: 6 amino acids
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO: 5:

```
Glu Asn Ile Thr Asp Gly
1               5
```

(2) INFORMATION FOR SEQ ID NO: 6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO: 6:

AGCTCCTCCA TCAGTATTAT TTY        23